US012623044B2

(12) United States Patent
He et al.

(10) Patent No.: US 12,623,044 B2
(45) Date of Patent: May 12, 2026

(54) SAFETY VALVE SHEET, BREATHING TUBE, BREATHING TUBE ASSEMBLY AND BREATHING MASK

(71) Applicant: BMC MEDICAL CO., LTD., Beijing (CN)

(72) Inventors: Long He, Beijing (CN); Mingzhao Zhou, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 924 days.

(21) Appl. No.: 17/790,141

(22) PCT Filed: Dec. 28, 2020

(86) PCT No.: PCT/CN2020/140021
§ 371 (c)(1),
(2) Date: Jun. 30, 2022

(87) PCT Pub. No.: WO2021/136153
PCT Pub. Date: Jul. 8, 2021

(65) Prior Publication Data
US 2023/0043056 A1 Feb. 9, 2023

(30) Foreign Application Priority Data

Dec. 31, 2019 (CN) .......................... 201911421000.8

(51) Int. Cl.
*A61M 16/20* (2006.01)
*A61M 16/00* (2006.01)
(Continued)

(52) U.S. Cl.
CPC ........ *A61M 16/20* (2013.01); *A61M 16/0003* (2014.02); *A61M 16/06* (2013.01);
(Continued)

(58) Field of Classification Search
CPC . A61B 5/0876; A61M 11/001; A61M 11/002; A61M 15/0015; A61M 15/0016;
(Continued)

(56) References Cited

U.S. PATENT DOCUMENTS 5,647,355 A * 7/1997 Starr ................... A61M 16/208
128/205.24
5,738,087 A 4/1998 King
(Continued)

FOREIGN PATENT DOCUMENTS

CN 206304202 U 7/2017
CN 109568756 A 4/2019
(Continued)

*Primary Examiner* — Annette Dixon
(74) *Attorney, Agent, or Firm* — Bayramoglu Law Offices LLC

(57) ABSTRACT
A safety valve sheet, a breathing tube, a breathing tube assembly and a breathing mask are provided. The safety valve sheet is used for being arranged in the breathing tube which is provided with a safety valve hole of the breathing mask, the safety valve sheet comprises a sheet body, and the sheet body comprises an outer side surface being capable of covering the safety valve hole, wherein a protrusion is formed on the outer side surface, and the protrusion is used for being contacted with an inner side surface of a hole edge of the safety valve hole when the sheet body covers the safety valve hole to form an exhaust gap between the outer side surface and the hole edge. The safety valve sheet is simple in structure and can effectively reduce exhaust noise after being applied to the breathing mask.

12 Claims, 16 Drawing Sheets

(51) Int. Cl.
    *A61M 16/06*         (2006.01)
    *A61M 16/08*         (2006.01)

(52) U.S. Cl.
    CPC .... *A61M 16/0816* (2013.01); *A61M 16/0875*
        (2013.01); *A61M 16/0605* (2014.02); *A61M*
            *16/0633* (2014.02); *A61M 2202/0225*
        (2013.01); *A61M 2205/0216* (2013.01); *A61M*
        *2205/42* (2013.01); *A61M 2207/10* (2013.01)

(58) Field of Classification Search
    CPC ............ A61M 15/0018; A61M 15/008; A61M
               15/0086; A61M 15/009; A61M 15/0098;
               A61M 16/0057; A61M 16/0093; A61M
               16/06; A61M 16/0611; A61M 16/0616;
               A61M 16/0622; A61M 16/0633; A61M
               16/0644; A61M 16/0683; A61M 16/08;
               A61M 16/0816; A61M 16/0825; A61M
               16/0841; A61M 16/0875; A61M 16/105;
               A61M 16/1055; A61M 16/1065; A61M
               16/20; A61M 16/208; A61M 16/209;
               A61M 2016/0024; A61M 2016/0042;
               A61M 2039/244; A61M 2205/0216;
               A61M 2205/332; A61M 2205/42; A61M
               2205/584; A61M 2210/0618; A61M
               2230/60; A61M 2230/63; A62B 7/12;
               G01F 1/28; Y10T 137/7898; Y10T
                          137/7903
    See application file for complete search history.

(56) References Cited

U.S. PATENT DOCUMENTS

| | | | |
|---|---|---|---|
| 8,061,355 B2 * | 11/2011 | Jaffre | .................... A61M 16/08 |
| | | | 128/205.24 |
| 11,617,852 B2 * | 4/2023 | Gardein | ............ A61M 16/0816 |
| | | | 128/202.27 |
| 12,005,193 B2 * | 6/2024 | Nelson | .................. A61M 16/06 |
| 2004/0094157 A1 * | 5/2004 | Dantanarayana | ............................ |
| | | | A61M 16/0875 |
| | | | 128/207.12 |
| 2015/0059763 A1 * | 3/2015 | Chien | ............... A61M 16/0683 |
| | | | 128/206.26 |
| 2015/0114504 A1 | 4/2015 | Cecka et al. | |
| 2015/0136137 A1 | 5/2015 | Bugamelli et al. | |
| 2016/0129214 A1 | 5/2016 | Dantanarayana et al. | |
| 2017/0049988 A1 | 2/2017 | Dantanarayana et al. | |

FOREIGN PATENT DOCUMENTS

| | | |
|---|---|---|
| CN | 209361567 U | 9/2019 |
| CN | 209734715 U | 12/2019 |
| CN | 110975096 A | 4/2020 |
| CN | 211561463 U | 9/2020 |
| JP | 2008264566 A | 11/2008 |
| JP | 2008540056 A | 11/2008 |
| WO | 2018203759 A1 | 11/2018 |

* cited by examiner

SAFETY VALVE SHEET, BREATHING TUBE, BREATHING TUBE ASSEMBLY AND BREATHING MASK

CROSS REFERENCE TO RELEVANT APPLICATIONS

This application is the national phase entry of International Application No. PCT/CN2020/140021, filed on Dec. 28, 2020, which is based upon and claims priority to Chinese Patent Application No. 201911421000.8, filed on Dec. 31, 2019; the entire contents of which are incorporated herein by reference.

TECHNICAL FIELD

The present disclosure relates to the field of medical instruments, and more particularly, to a safety valve sheet, a breathing tube, a breathing tube assembly and a breathing mask.

BACKGROUND

At present, full-face mask on the market may be classified into an exhausted mask and a non-exhausted mask according to different exhaust modes. The exhausted mask is connected to a pressure support device such as a ventilator through a conduit, so as to connect a gas pressure provided by, for example, the ventilator with an airway of a patient. The exhausted mask is provided with a special exhaust hole at a mask end, so as to facilitate exhausting breathing exhaust gas. In addition, in order to prevent suffocation in the case that the ventilator fails or the conduit is blocked, the full-face mask is usually provided with a safety valve hole. A safety valve sheet is arranged at the safety valve hole inside the exhausted mask. For example, there are two existing exhaust schemes for the full-face mask. In one scheme, the exhaust hole and the safety valve hole are both arranged in a bent tube of the mask. In the other scheme, the exhaust hole is arranged in a frame of the mask, and the safety valve hole is arranged in the bent tube.

In this way, when the ventilator works normally, there are an inspiration state and an expiration state. In the inspiration state, an air pressure pushes up the safety valve sheet to block the safety valve hole. Some air flow from the ventilator is delivered to the patient, and some air flow is exhausted through the exhaust hole. In the expiration state, the air pressure pushes up the safety valve sheet to block the safety valve hole. The air flow from the ventilator and the exhaust gas expired by the patient are exhausted through the exhaust hole. When the ventilator has a single failure or the conduit of the ventilator is blocked, the safety valve sheet is recovered to a stretched state due to its own elasticity, thus blocking the conduit of the ventilator and opening the safety valve hole. The patient may breathe through the exhaust hole and the safety valve hole to prevent suffocation.

However, the current structure also has some shortcomings. For example, most patients use the mask for a long time in a quiet environment at night, but the mask makes loud noise during exhausting, which usually affects the sleep quality of the patients and bed partners of the patients. For another example, the mask or the bent tube has a large volume, a complex structure, and relatively high material cost and economic cost.

SUMMARY

In a first aspect, the present disclosure aims to provide a safety valve sheet, and the safety valve sheet is simple in structure and can effectively reduce exhaust noise after being applied to a breathing mask.

In order to achieve the above object, the present disclosure provides a safety valve sheet, and the safety valve sheet is used for being arranged in a breathing tube which is provided with a safety valve hole of a breathing mask, wherein the safety valve sheet includes a sheet body, and the sheet body includes an outer side surface being capable of covering the safety valve hole, wherein a protrusion is formed on the outer side surface, and the protrusion is used for being contacted with an inner side surface of a hole edge of the safety valve hole when the sheet body covers the safety valve hole to form an exhaust gap between the outer side surface and the hole edge. In the technical solution, the protrusion is formed on the outer side surface of the sheet body of the safety valve sheet, so that after the safety valve sheet is applied to the breathing tube of the breathing mask, the safety valve sheet will cover the safety valve hole during normal inspiration and expiration of a user through the breathing mask. At the moment, the protrusion is contacted with the inner side surface of the hole edge of the safety valve hole, so that the exhaust gap is formed between the outer side surface of the safety valve sheet and the hole edge, and exhaust gas expired by the user will be exhausted through the exhaust gap, thus reducing exhaust noise. In addition, it is not necessary to arrange an additional exhaust structure on the breathing tube of the breathing mask, so that the breathing mask is simple in structure, thus reducing a cost.

Further, the sheet body is a flexible body.

Further, a height of the protrusion relative to the outer side surface ranges from 0.1 mm to 1.2 mm; and/or, a plurality of protrusions are provided and arranged at intervals.

In a second aspect, the present disclosure provides a breathing tube, and the breathing tube is simple in structure and can effectively reduce exhaust noise after being applied to a breathing mask.

Therefore, the breathing tube provided in the aspect is used for being connected to an air cavity cover of a breathing mask, wherein a safety valve hole is formed in a tube wall of the breathing tube, a protrusion is formed on an inner side surface of a hole edge of the safety valve hole, and the protrusion is used for being contacted with an outer side surface of a safety valve sheet when the safety valve sheet covers the safety valve hole inside the breathing tube to form an exhaust gap between the outer side surface and the hole edge. In the technical solution, the protrusion is formed on the inner side surface of the hole edge of the safety valve hole, so that after the safety valve sheet is arranged in the breathing tube, the safety valve sheet will cover the safety valve hole during normal inspiration and expiration of a user through the breathing mask. At the moment, the protrusion is contacted with the outer side surface of the safety valve sheet, so that the exhaust gap is formed between the outer side surface of the safety valve sheet and the hole edge, and exhaust gas expired by the user will be exhausted through the exhaust gap, thus reducing exhaust noise. In addition, it is not necessary to arrange an additional exhaust structure on the breathing tube of the breathing mask, so that the breathing mask is simple in structure, thus reducing a cost.

Further, a height of the protrusion relative to the inner side surface of the hole edge ranges from 0.1 mm to 1.2 mm; and/or, a plurality of protrusions are provided and arranged at intervals along a circumferential direction of the hole edge.

In a third aspect, the present disclosure provides a breathing tube assembly, and the breathing tube assembly is simple in structure and can effectively reduce exhaust noise after being applied to a breathing mask.

Therefore, the breathing tube assembly provided by the present disclosure includes a breathing tube and a safety valve sheet, wherein a safety valve hole is formed in a tube wall of the breathing tube, and the safety valve sheet is capable of being movably arranged in the breathing tube; and the safety valve sheet includes a covering state being capable of covering the safety valve hole and an opening state being capable of opening the safety valve hole; wherein, in the covering state, an exhaust gap is arranged between the safety valve sheet and a hole edge of the safety valve hole. In the technical solution, in the covering state, the exhaust gap is arranged between the safety valve sheet and the hole edge of the safety valve hole, so that after the breathing tube is connected to an air cavity cover of the breathing mask, the safety valve sheet will cover the safety valve hole during normal inspiration and expiration of a user through the breathing mask. At the moment, the exhaust gap is arranged between the safety valve sheet and the hole edge of the safety valve hole, so that exhaust gas expired by the user will be exhausted through the exhaust gap, thus reducing exhaust noise. In addition, it is not necessary to arrange an additional exhaust structure on the breathing tube of the breathing mask, so that the breathing mask is simple in structure, thus reducing a cost.

Further, the safety valve sheet is any safety valve sheet in the first aspect above, and/or, the breathing tube is any breathing tube in the second aspect above.

In a fourth aspect, the present disclosure provides a breathing tube assembly, and the breathing tube assembly is simple in structure and can effectively reduce exhaust noise after being applied to a breathing mask. Therefore, the breathing tube assembly provided by the present disclosure includes a breathing tube and a safety valve sheet, wherein a plurality of exhaust holes arranged at intervals are formed in a tube wall of the breathing tube, and the safety valve sheet is capable of being movably arranged in the breathing tube; and the safety valve sheet includes a covering state being capable of covering at least some of the exhaust holes and an opening state being capable of opening the covered exhaust holes. In the technical solution, the safety valve sheet covers some of the exhaust holes in the covering state, so that after the breathing tube is connected to an air cavity cover of the breathing mask, the safety valve sheet will cover some of the exhaust holes during normal inspiration and expiration of a user through the breathing mask. At the moment, exhaust gas expired by the user will be exhausted from other exhaust holes not covered by the safety valve sheet, thus reducing exhaust noise. In addition, it is not necessary to arrange an additional exhaust structure on the breathing tube of the breathing mask, so that the breathing mask is simple in structure, thus reducing a cost.

Further, the exhaust holes are circular holes or strip holes.

In a fifth aspect, the present disclosure provides a breathing tube assembly, and the breathing tube assembly is simple in structure and can effectively reduce exhaust noise after being applied to a breathing mask.

Therefore, the breathing tube assembly provided by the present disclosure includes a breathing tube and a safety valve sheet, wherein a safety valve hole and a plurality of exhaust holes arranged at intervals around the safety valve hole are formed in a tube wall of the breathing tube, and the safety valve sheet is capable of being movably arranged in the breathing tube; and the safety valve sheet includes a covering state being capable of covering the safety valve hole and an opening state being capable of opening the safety valve hole. In the technical solution, the plurality of exhaust holes are arranged at intervals around the safety valve hole, so that after the breathing tube is connected to an air cavity cover of the breathing mask, the safety valve sheet will cover the safety valve hole during normal inspiration and expiration of a user through the breathing mask. At the moment, exhaust gas expired by the user will be exhausted from the plurality of exhaust holes around the safety valve hole, thus reducing exhaust noise. In addition, it is not necessary to arrange an additional exhaust structure on the breathing tube of the breathing mask, so that the breathing mask is simple in structure, thus reducing a cost.

Further, the exhaust holes are circular holes or strip holes; and/or, in the covering state, an exhaust gap is formed between an outer side surface of the safety valve sheet and a hole edge of the safety valve hole.

In a sixth aspect, the present disclosure provides a safety valve sheet, and the safety valve sheet is simple in structure and can effectively reduce exhaust noise after being applied to a breathing mask. Therefore, the safety valve sheet provided by the present disclosure is used for being arranged in a breathing tube which is provided with a safety valve hole in a breathing mask, wherein the safety valve sheet includes a sheet body being capable of covering the safety valve hole, and a plurality of exhaust holes arranged at intervals are formed in the sheet body. In the technical solution, the plurality of exhaust holes arranged at intervals are formed in the sheet body, so that after the safety valve sheet is applied to the breathing tube of the breathing mask, the safety valve sheet will cover the safety valve hole during normal inspiration and expiration of a user through the breathing mask. At the moment, exhaust gas expired by the user will be exhausted from the plurality of exhaust holes in the sheet body, thus reducing exhaust noise. In addition, it is not necessary to arrange an additional exhaust structure on the breathing tube of the breathing mask, so that the breathing mask is simple in structure, thus reducing a cost. Further, the sheet body is a flexible body.

In a seventh aspect, the present disclosure provides a breathing tube assembly, and the breathing tube assembly includes a breathing tube and any safety valve sheet in the sixth aspect above, wherein a safety valve hole is formed in a tube wall of the breathing tube, and the safety valve sheet is capable of being movably arranged in the breathing tube; and the safety valve sheet includes a covering state being capable of covering the safety valve hole and an opening state being capable of opening the safety valve hole. As described above, the breathing tube assembly is simple in structure and can effectively reduce exhausting noise after being applied to the breathing mask.

Further, in the covering state, an exhaust gap is formed between an outer side surface of the safety valve sheet and a hole edge of the safety valve hole.

In an eighth aspect, the present disclosure provides a breathing mask, which includes an air cavity cover and a breathing tube assembly, wherein the breathing tube assembly is any breathing tube assembly in the third aspect above; or, the breathing tube assembly is any breathing tube assembly in the fourth aspect above; or, the breathing tube assembly is any breathing tube assembly in the fifth aspect above; or, the breathing tube assembly is any breathing tube assembly in the seventh aspect above, wherein one end of the breathing tube is connected to the air cavity cover. In this way, as described above, the breathing mask is simple in structure and can effectively reduce exhaust noise.

REFERENCE NUMERALS

1 refers to safety valve sheet, 2 refers to breathing mask, 3 refers to safety valve hole, 4 refers to breathing tube, 5 refers to sheet body, 6 refers to outer side surface, 7 refers to protrusion, 8 refers to hole edge, 9 refers to exhaust gap, 10 refers to air cavity cover, 11 refers to exhaust hole, 12 refers to breathing tube assembly, 13 refers to forehead pad, 14 refers to liner, and 15 refers to mask frame.

DETAILED DESCRIPTION OF THE
EMBODIMENTS

It should be noted that, in the case of no conflict, the embodiments in the present disclosure and the features in the embodiments may be combined with each other. The present disclosure will be described in detail hereinafter with reference to the drawings and the embodiments.

Figure 1:
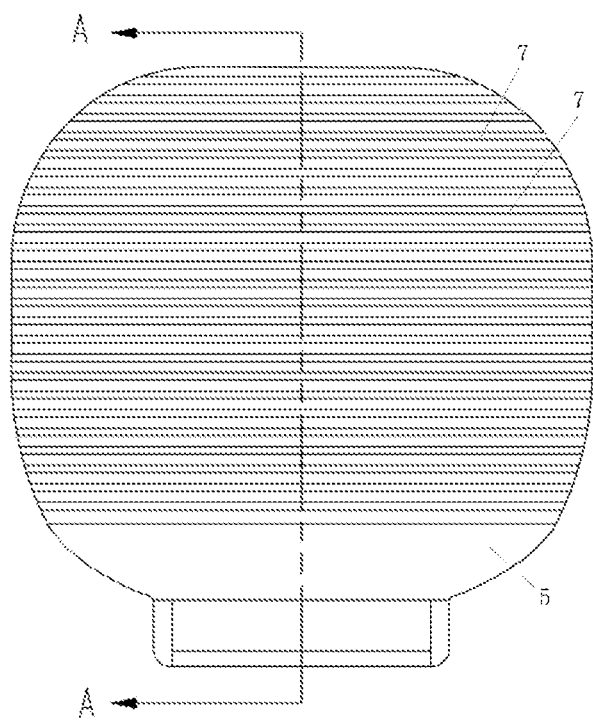
FIG. 1 is a front structural diagram of a first safety valve sheet provided by a specific embodiment of the present disclosure.
Figure 2:
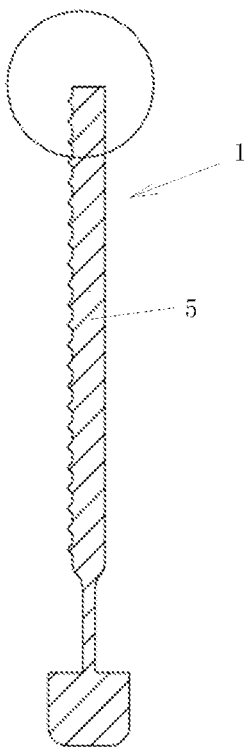
FIG. 2 is a cross-sectional view of an A-A line in FIG. 1.
Figure 3:
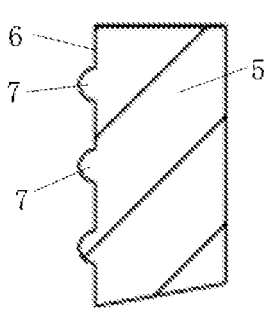
FIG. 3 is an enlarged structural diagram of a circle part in FIG. 2.
Figure 4:
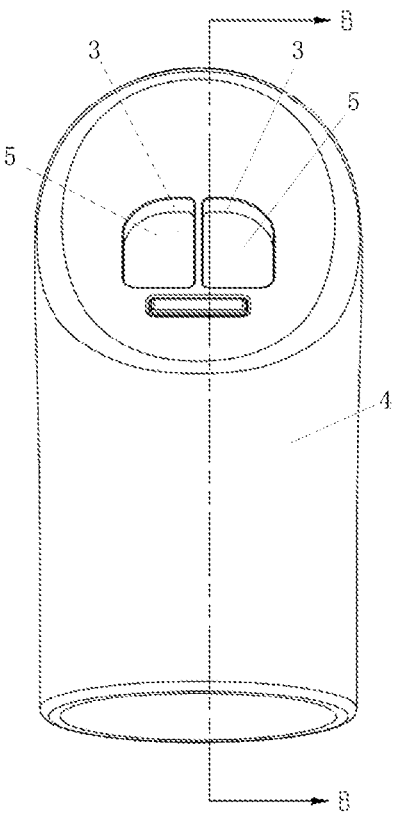
FIG. 4 is a schematic structural diagram of a first breathing tube assembly provided by a specific embodiment of the present disclosure, and shows the safety valve sheet in FIG. 1.
Figure 5:
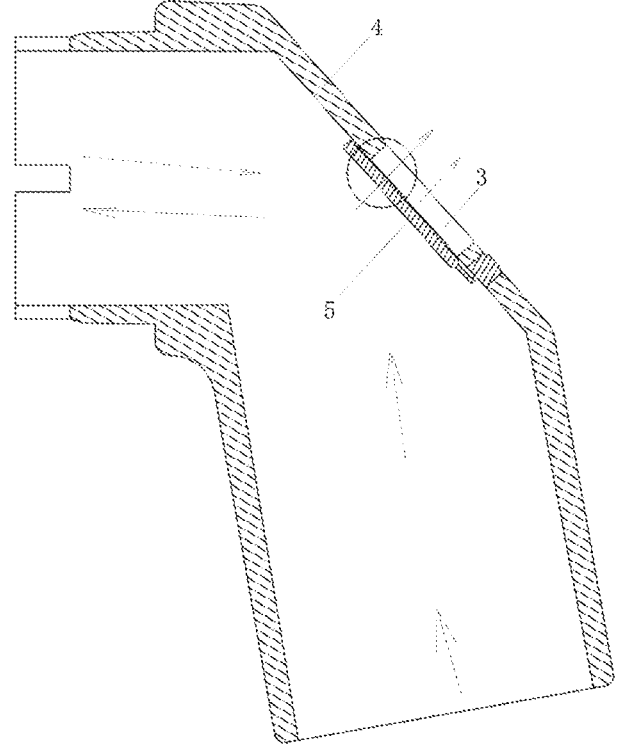
FIG. 5 is a cross-sectional view of a B-B line in FIG. 4, wherein the safety valve sheet is in a covering state.
Figure 6:
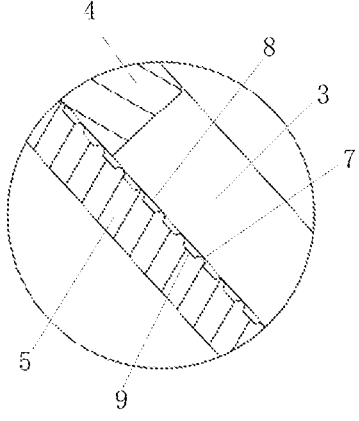
FIG. 6 is an enlarged structural diagram of a circle part in FIG. 5.
Figure 7:
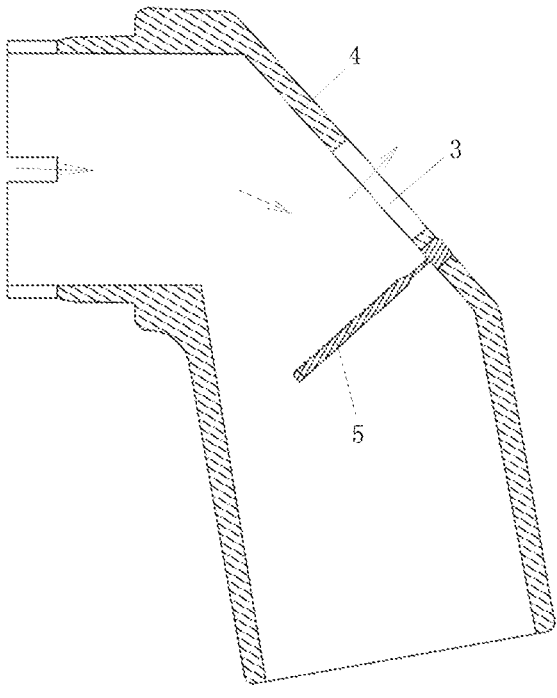
FIG. 7 is a schematic diagram of the safety valve sheet in FIG. 5 in an opening state.

In a first aspect, with reference to FIG. 1, FIG. 2 and FIG. 3, a first safety valve sheet 1 provided by the present disclosure is used for being arranged in a breathing tube 4 which is provided with a safety valve hole 3 of a breathing mask 2. As shown in FIG. 5 to FIG. 7, the safety valve sheet includes a sheet body 5, the sheet body 5 includes an outer side surface 6 being capable of covering the safety valve hole 3, wherein a protrusion 7 is formed on the outer side surface 6, and the protrusion 7 is used for being contacted with an inner side surface of a hole edge 8 of the safety valve hole 3 when the sheet body 5 covers the safety valve hole 3 to form an exhaust gap 9 between the outer side surface 6 and the hole edge 8. In the technical solution, the protrusion is formed on the outer side surface of the sheet body of the safety valve sheet, so that after the safety valve sheet is applied to the breathing tube of the breathing mask, the safety valve sheet will cover the safety valve hole during normal inspiration and expiration of a user through the breathing mask. At the moment, the protrusion is contacted with the inner side surface of the hole edge of the safety valve hole, so that the exhaust gap is formed between the outer side surface of the safety valve sheet and the hole edge, and exhaust gas expired by the user will be exhausted through the exhaust gap, thus realizing low-flow exhaust and reducing exhaust noise. In addition, it is not necessary to arrange an additional exhaust structure on the breathing tube of the breathing mask, so that the breathing tube is simple in structure, and a plastic mold for manufacturing the breathing tube is simple in structure, thus reducing an industrial cost, further simplifying a structure of the breathing mask, and reducing a cost.

In addition, as shown in FIG. 1 and FIG. 2, the safety valve sheet 1 includes a clamping block for connection which is connected onto the sheet body 5, and the clamping block for connection is connected to the sheet body 5 through a transitional connecting sheet, wherein a thickness of the transitional connecting sheet is smaller than those of the sheet body 5 and the clamping block for connection, so that the clamping block for connection may be clamped in a bayonet located below the safety valve hole on a tube wall of the breathing tube, as shown in FIG. 5, thus the sheet body 5 may be connected in the breathing tube 4. Certainly, it should be understood that a connection mode between the safety valve sheet 1 and the breathing tube 4 is not limited to this. For example, a flange is formed at one end of the sheet body 5, and the flange may be adhered to an inner surface of the breathing tube 4 or connected onto the inner surface of the breathing tube 4 by a screw or other fasteners.

In an embodiment, the sheet body 5 may be a rigid body made of a rigid material. At the moment, the aforementioned transitional connecting sheet may have an elasticity, so that in the case of no effect of an air pressure from, for example, a ventilator, the sheet body 5 may be automatically and elastically recovered from a covering state of covering the safety valve hole to an opening state of opening the safety valve hole, such as converting from the state shown in FIG. 5 to the state shown in FIG. 7.

In another embodiment, the sheet body 5 is a flexible body. For example, the aforementioned clamping block for connection and the aforementioned transitional connecting sheet are integrally formed with the sheet body 5 into the flexible body. For example, the flexible body may be made of a flexible material such as silica gel, or the flexible body may be a flexible elastic sheet having a surface layer covered with soft rubber. In this way, the flexible body, such as the soft silica gel or the soft rubber surface layer of the flexible elastic sheet, can slow down air flow vibration, thus further reducing the exhaust noise.

In addition, in the safety valve sheet 1, the protrusion 7 may be in any shape, such as a point-ball shape, a rectangular platform shape or a circular platform shape. In addition, one or a plurality of protrusions 7 arranged at intervals may be provided. For example, the plurality of protrusions 7 are distributed on the outer side surface 6 of the sheet body in a dot matrix, a linear type, a divergent type, an annular shape or any other distribution forms. The outer side surface 6 may be understood as: a side surface of the safety valve sheet 1 contacted with an inner surface of the breathing tube such as a bent tube after being pushed up by an air flow from, for example, the ventilator.

In addition, a height of the protrusion 7 relative to the outer side surface 6 ranges from 0.1 mm to 1.2 mm, so that the exhaust gap 9 may be as small as possible while meeting exhaust, so as to further reduce the exhaust noise. Preferably, the height of the protrusion 7 relative to the outer side surface 6 ranges from 0.2 mm to 0.8 mm. More preferably, the height of the protrusion 7 relative to the outer side surface 6 is 0.5 mm. Certainly, it should be understood that the height of the protrusion 7 relative to the outer side surface 6 is not limited to this. If necessary, the height may be any other numerical value, which will not be listed herein.

Figure 8:
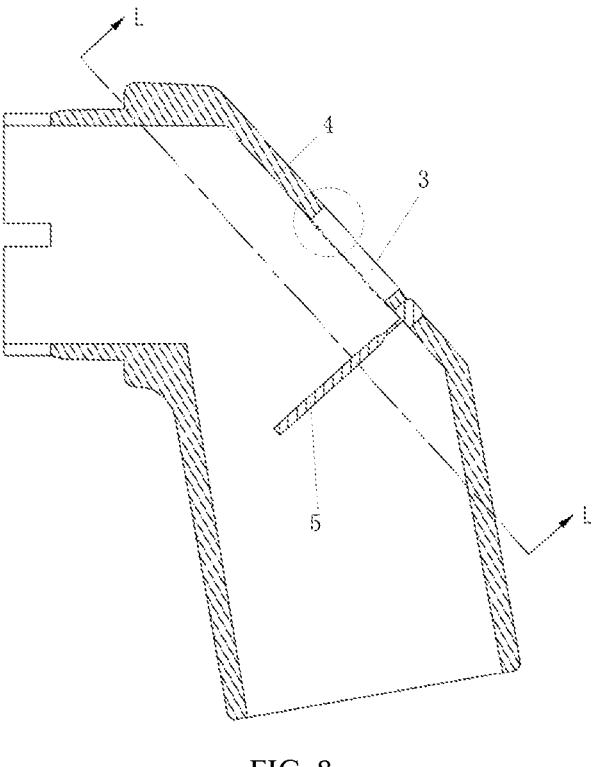
FIG. 8 is a cross-sectional structural diagram of a second breathing tube assembly provided by a specific embodiment of the present disclosure, wherein the safety valve sheet is in the opening state.
Figure 9:
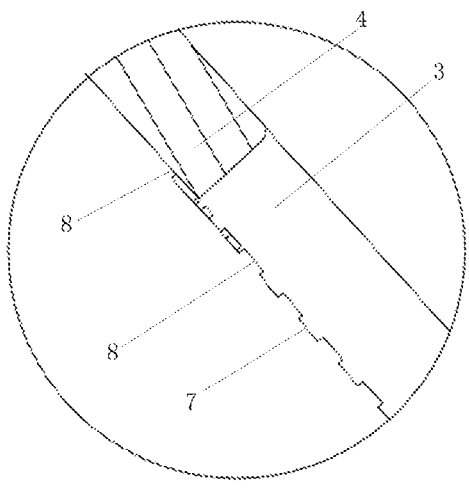
FIG. 9 is a locally enlarged view of a circle part in FIG. 8.
Figure 10:
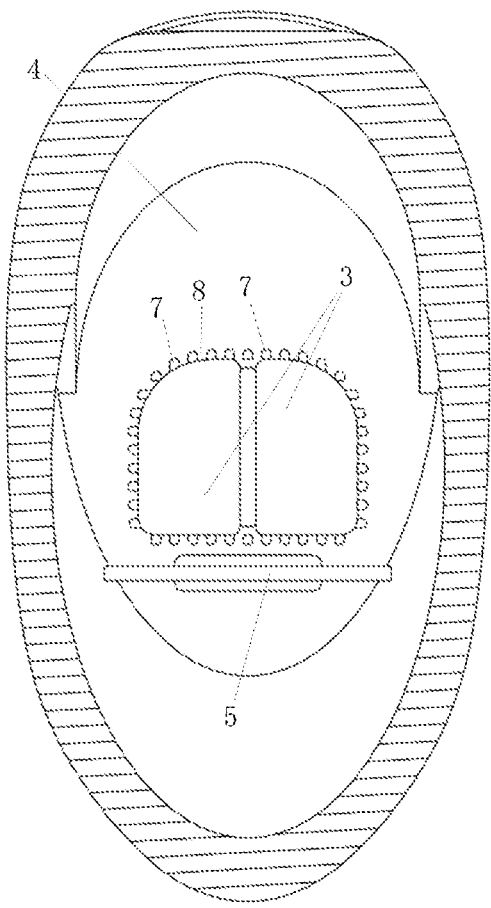
FIG. 10 is a cross-sectional view of an L-L line in FIG. 8.
Figure 27:
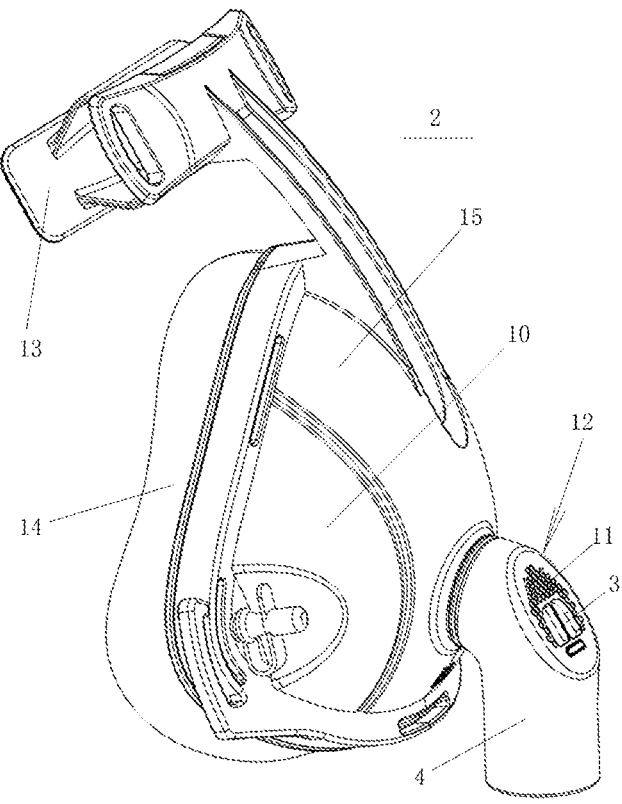
FIG. 27 is a schematic structural diagram of a breathing mask provided by a specific embodiment of the present disclosure.

In a second aspect, with reference to FIG. 8, FIG. 9 and FIG. 10, a breathing tube 4 provided by the present disclosure is used for being connected to an air cavity cover 10 of a breathing mask 2. As shown in FIG. 27, a safety valve hole 3 is formed in a tube wall of the breathing tube 4, wherein a protrusion 7 is formed on an inner side surface of a hole edge 8 of the safety valve hole 3, and the protrusion 7 is used for being contacted with an outer side surface 6 of a safety valve sheet 1 when the safety valve sheet covers the safety valve hole 3 inside the breathing tube so as to form an exhaust gap 9 between the outer side surface 6 and the hole edge 8. In the technical solution, the protrusion is formed on the inner side surface of the hole edge of the safety valve hole, so that after the safety valve sheet is arranged in the breathing tube, the safety valve sheet will cover the safety valve hole during normal inspiration and expiration of a user through the breathing mask. At the moment, the protrusion is contacted with the outer side surface of the safety valve sheet, so that the exhaust gap is formed between the outer side surface of the safety valve sheet and the hole edge, and exhaust gas expired by the user will be exhausted through the exhaust gap, thus realizing low-flow exhaust and reducing exhaust noise. Therefore, the breathing tube is simple in structure, and can effectively reduce the exhaust noise after being applied to the breathing mask. In addition, it is not necessary to arrange an additional exhaust structure on the breathing tube of the breathing mask, so that the breathing tube is simple in structure, and a plastic mold for manufacturing the breathing tube is simple in structure, thus reducing an industrial cost, further simplifying a structure of the breathing mask, and reducing a cost.

In addition, a height of the protrusion 7 relative to the inner side surface of the hole edge 8 ranges from 0.1 mm to 1.2 mm, so that the exhaust gap 9 may be as small as possible while meeting exhaust, so as to further reduce the exhaust noise. Preferably, the height of the protrusion 7 relative to the inner side surface of the hole edge 8 ranges from 0.2 mm to 0.8 mm. More preferably, the height of the protrusion 7 relative to the inner side surface of the hole edge 8 is 0.5 mm. Certainly, it should be understood that the height of the protrusion 7 relative to the inner side surface of the hole edge 8 is not limited to this. If necessary, the height may be any other numerical value, which will not be listed herein.

In addition, in the breathing tube 4, the protrusion 7 may be in any shape, such as a point-ball shape, a rectangular platform shape or a circular platform shape. In addition, one or a plurality of protrusions 7 arranged at intervals along a circumferential direction of the hole edge may be provided. For example, the plurality of protrusions 7 are arranged at intervals along the circumferential direction of the hole edge in a dot matrix, a linear type, a divergent type, an annular shape or any other distribution forms.

In addition, the breathing tube 4 may be a bent tube, a straight tube, or other curved tubes, which may be selected according to actual requirements.

In a third aspect, the present disclosure provides a breathing tube assembly. With reference to FIG. 5, FIG. 7 and FIG. 8, the breathing tube assembly includes a breathing tube 4 and a safety valve sheet 1, wherein a safety valve hole 3 is formed in a tube wall of the breathing tube 4, and the safety valve sheet 1 is capable of being movably arranged in the breathing tube 4. The safety valve sheet 1 includes a covering state being capable of covering the safety valve hole 3 and an opening state being capable of opening the safety valve hole 3; wherein, in the covering state, an exhaust gap 9 is arranged between the safety valve sheet 1 and a hole edge of the safety valve hole 3. In the technical solution, in the covering state, the exhaust gap is arranged between the safety valve sheet and the hole edge of the safety valve hole, so that after the breathing tube is connected to an air cavity cover of the breathing mask, the safety valve sheet will cover the safety valve hole during normal inspiration and expiration of a user through the breathing mask. At the moment, the exhaust gap is arranged between the safety valve sheet and the hole edge of the safety valve hole, so that exhaust gas expired by the user will be exhausted through the exhaust gap, thus realizing low-flow exhaust and reducing exhaust noise. In addition, it is not necessary to arrange an additional exhaust structure on the breathing tube of the breathing mask, so that the breathing tube is simple in structure, and a plastic mold for manufacturing the breathing tube is simple in structure, thus reducing an industrial cost, further simplifying a structure of the breathing mask, and reducing a cost.

It should be noted that, in the breathing tube assembly in the third aspect, the exhaust gap 9 may be formed in various ways. For example, in one way, the safety valve sheet 1 and the tube wall of the breathing tube 4 are connected by a connecting structure, and the safety valve sheet 1 rotates towards the safety valve hole 3 under an effect of an air pressure from, for example, a ventilator, so that the connecting structure will block the safety valve sheet 1 from rotating continuously when the safety valve sheet is about to cover the safety valve hole 3, thus forming the exhaust gap 9 between the safety valve sheet 1 and the hole edge of the safety valve hole 3. Alternatively, in another way, the safety valve sheet 1 is any safety valve sheet in the first aspect above (such as a structure shown in FIG. 5 to FIG. 7), and/or, the breathing tube 4 is any breathing tube in the second aspect above (such as a structure shown in FIG. 8 to FIG. 10). In this way, one end of the breathing tube 4 of the breathing tube assembly is connected to the air cavity cover 10 of the breathing mask 2, and the other end of the breathing tube 4 is connected to a pressure support device such as the ventilator. For example, when the ventilator works normally, there are an inspiration state and an expiration state. When the user (patient) is in the inspiration state, the air pressure from the ventilator pushes up the safety valve sheet to cover the safety valve hole. Due to the existence of the exhaust gap, as shown by solid arrows in FIG. 5, most of an air flow from the ventilator is delivered to the patient, and a small part of the air flow is exhausted through the exhaust gap. When the user (patient) is in the expiration state, the air pressure from the ventilator pushes up the safety valve sheet to cover the safety valve hole. At the moment, the air flow from the ventilator and the exhaust gas expired by the patient are exhausted through the exhaust gap, as shown by dotted arrows in FIG. 5. In addition, for example, when the ventilator has a single failure or a conduit of the ventilator is blocked, the safety valve sheet may be converted from the covering state to the opening state. For example, the safety valve sheet is recovered to the opening state (stretched state) under its own elasticity, as shown in FIG. 7 or FIG. 8, so as to open the safety valve hole, so that the patient may breathe through the safety valve hole (as shown by solid arrows in FIG. 7) to prevent suffocation.

In a fourth aspect, the present disclosure provides a breathing tube assembly. With reference to FIG. 11 to FIG. 16, the breathing tube assembly includes a breathing tube 4 and a safety valve sheet 1, wherein a plurality of exhaust holes 11 arranged at intervals are formed in a tube wall of the breathing tube 4, and the safety valve sheet 1 is capable of being movably arranged in the breathing tube 4. The safety valve sheet 1 includes a covering state being capable of covering at least some of the exhaust holes 11 and an opening state being capable of opening the covered exhaust holes 11. In the technical solution, the safety valve sheet covers some of the exhaust holes in the covering state, so that after the breathing tube is connected to an air cavity cover of the breathing mask, the safety valve sheet will cover some of the exhaust holes during normal inspiration and expiration of a user through the breathing mask. At the moment, exhaust gas expired by the user will be exhausted from other exhaust holes not covered by the safety valve sheet, thus realizing low-flow exhaust and then reducing exhaust noise. In addition, it is not necessary to arrange an additional exhaust structure on the breathing tube of the breathing mask, so that the breathing tube is simple in structure, and a plastic mold for manufacturing the breathing tube is simple in structure, thus reducing an industrial cost, further simplifying a structure of the breathing mask, and reducing a cost.

Figure 11:
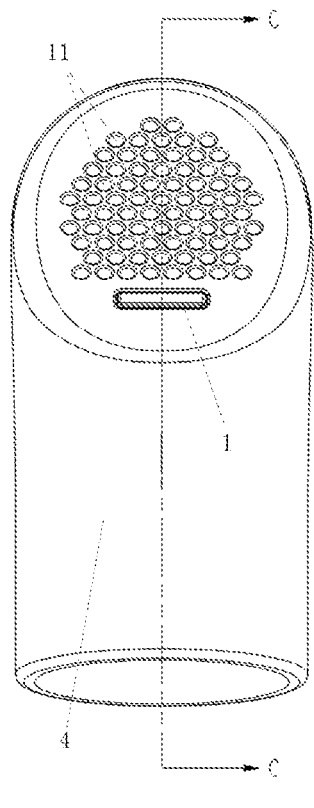
FIG. 11 is a schematic structural diagram of a third breathing tube assembly provided by a specific embodiment of the present disclosure.
Figure 12:
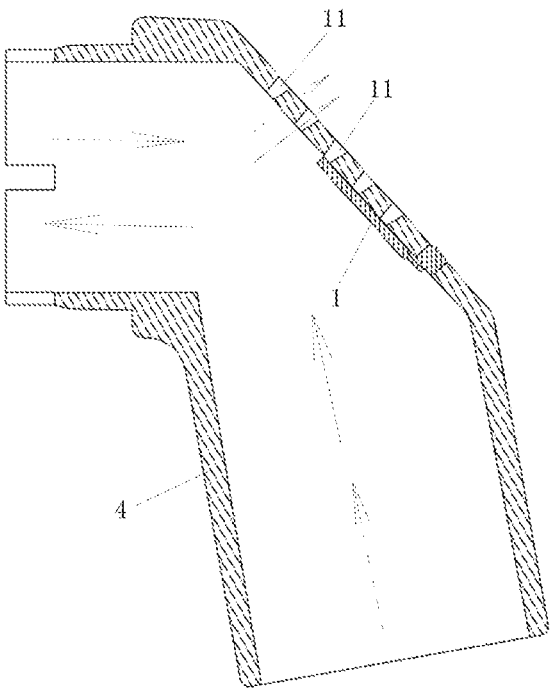
FIG. 12 is a cross-sectional view of a C-C line in FIG. 11, wherein the safety valve sheet is in the covering state.
Figure 13:
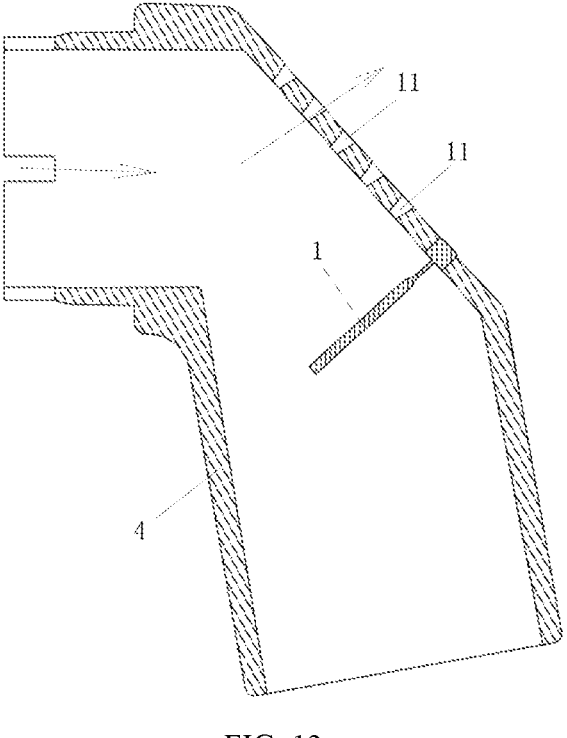
FIG. 13 is a schematic diagram of the safety valve sheet in FIG. 12 in the opening state.
Figure 14:
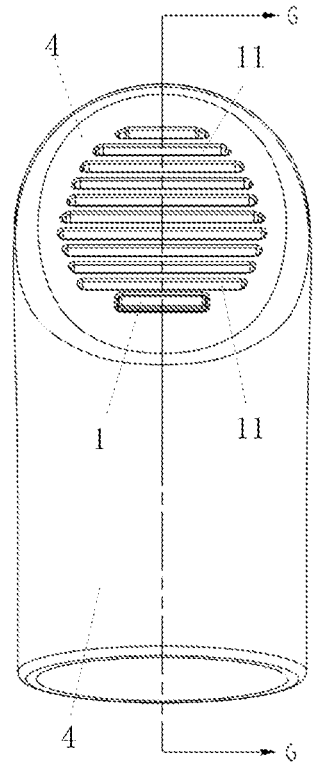
FIG. 14 is a schematic structural diagram of a fourth breathing tube assembly provided by a specific embodiment of the present disclosure.
Figure 15:
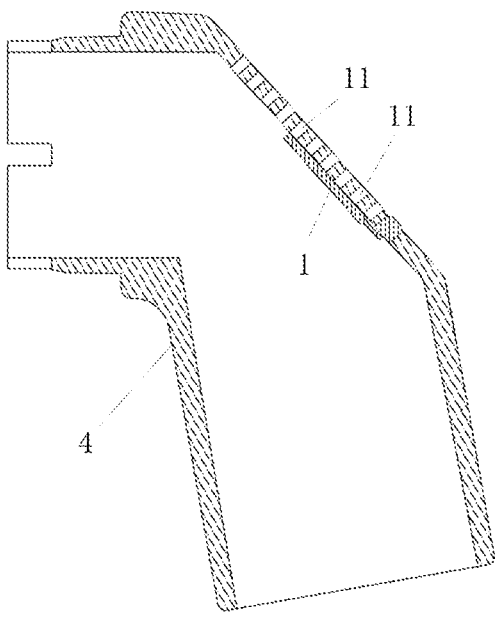
FIG. 15 is a cross-sectional view of a G-G line in FIG. 14, wherein the safety valve sheet is in the covering state.
Figure 16:
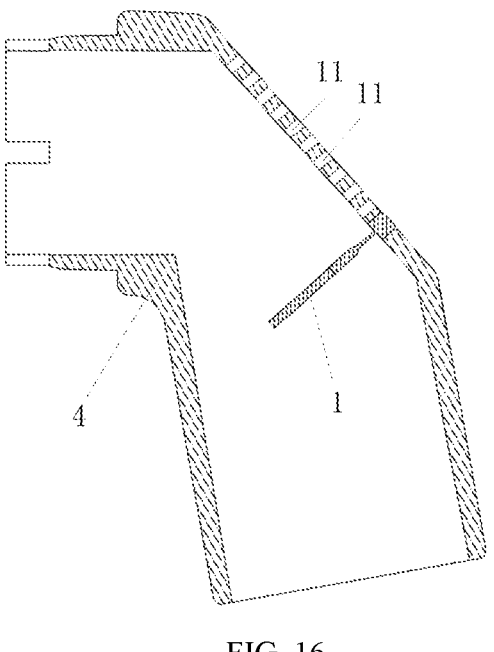
FIG. 16 is a schematic diagram of the safety valve sheet in FIG. 15 in the opening state.

It should be understood here that, in the breathing tube assembly, the exhaust holes 11 may be in various shapes and arranged in various ways. For example, as shown in FIG. 11 to FIG. 13, the exhaust holes 11 are circular holes, and arranged in rows and columns or arranged in an annular shape. Further, the exhaust holes 11 are small holes. Alternatively, as shown in FIG. 14 to FIG. 16, the exhaust holes 11 are strip holes, and arranged in rows. Certainly, the shape and the arrangement way of the exhaust holes 11 are not limited to this. In addition, as shown in FIG. 12, in a direction from inside to outside of the breathing tube 4, diameters of the exhaust holes 11 are gradually increased to form gradually enlarged holes, so that a flow rate of exhaust gas can be slowed down, thus further reducing exhaust noise. In this way, in FIG. 12, in the case of inspiration, as shown by solid arrows in FIG. 12, most of an air flow from, for example, the ventilator is delivered to the patient, and a small part of the air flow is exhausted from the other exhaust holes not covered by the safety valve sheet. In the case of expiration, as shown by dotted arrows in FIG. 12, the air flow from, for example, the ventilator and the exhaust gas expired by the patient are exhausted from the other exhaust holes not covered by the safety valve sheet. In addition, in FIG. 13, for example, when the ventilator has a single failure or a conduit of the ventilator is blocked, the safety valve sheet may be converted from the covering state to the opening state. For example, the safety valve sheet is recovered to the opening state (stretched state) under its own elasticity, so as to open all the exhaust holes, so that the patient may breathe through all the exhaust holes (as shown by solid arrows in FIG. 13) to prevent suffocation.

Figure 17:
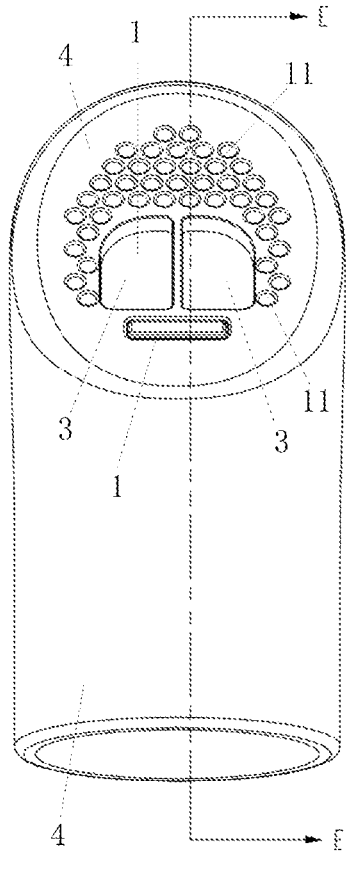
FIG. 17 is a schematic structural diagram of a fifth breathing tube assembly provided by a specific embodiment of the present disclosure.
Figure 18:
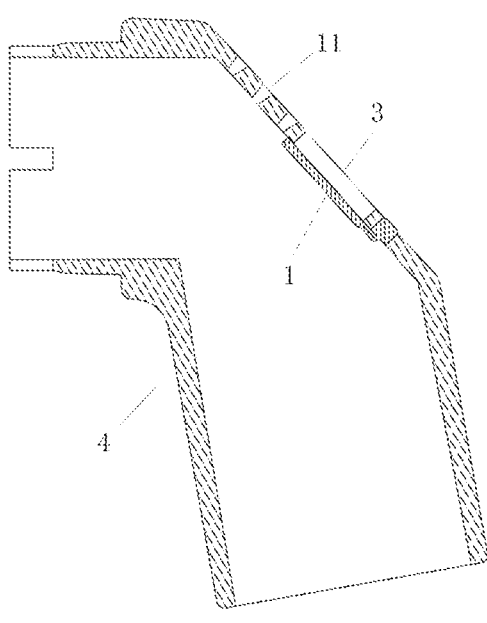
FIG. 18 is a cross-sectional view of an E-E line in FIG. 17, wherein the safety valve sheet is in the covering state.
Figure 19:
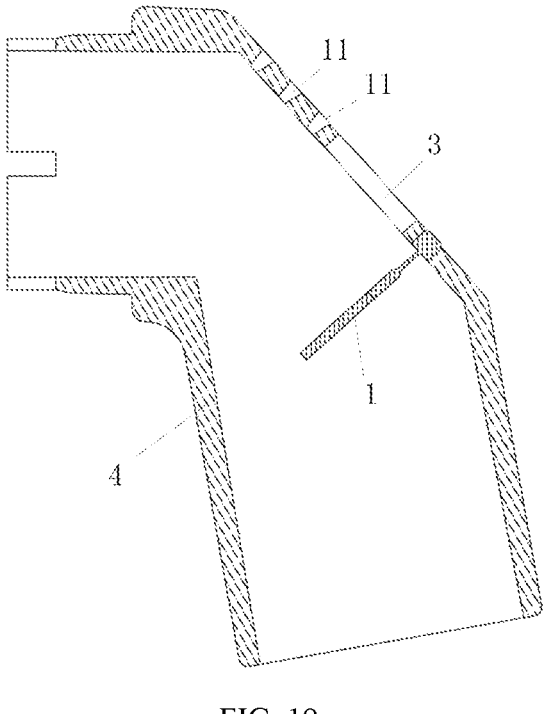
FIG. 19 is a schematic diagram of the safety valve sheet in FIG. 18 in the opening state.
Figure 20:
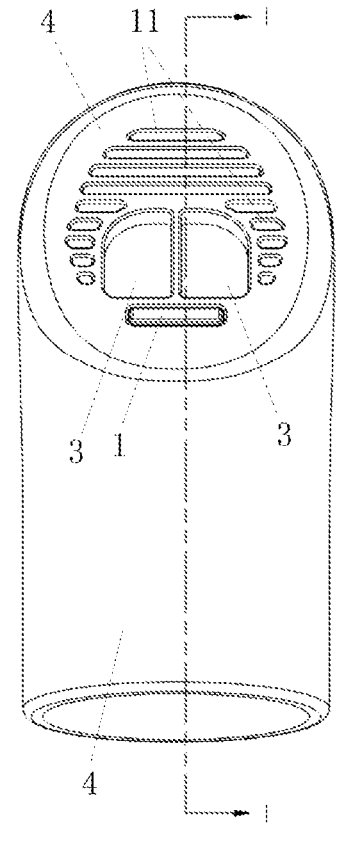
FIG. 20 is a schematic structural diagram of a sixth breathing tube assembly provided by a specific embodiment of the present disclosure.
Figure 21:
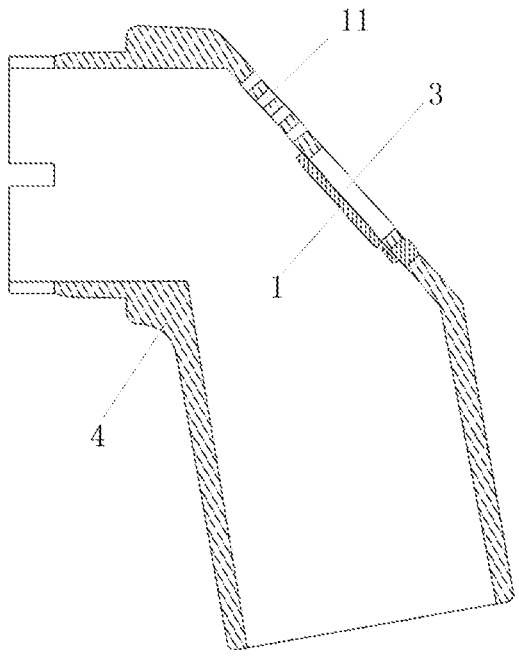
FIG. 21 is a cross-sectional view of an I-I line in FIG. 20, wherein the safety valve sheet is in the covering state.
Figure 22:
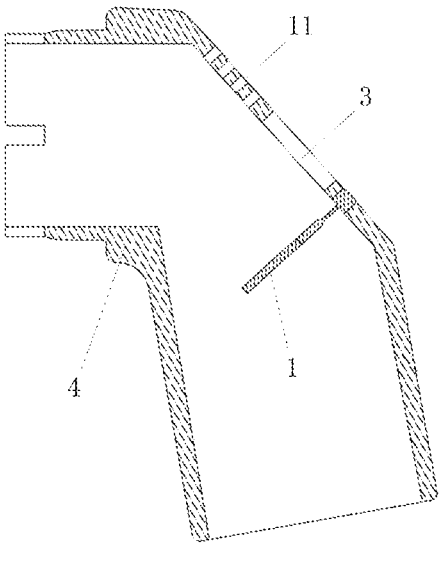
FIG. 22 is a schematic diagram of the safety valve sheet in FIG. 21 in the opening state.

In a fifth aspect, the present disclosure provides a breathing tube assembly. With reference to FIG. 17 to FIG. 22, the breathing tube assembly includes a breathing tube 4 and a safety valve sheet 1. A safety valve hole 3 and a plurality of exhaust holes 11 arranged at intervals around the safety valve hole 3 are formed in a tube wall of the breathing tube 4, and the safety valve sheet 1 is capable of being movably arranged in the breathing tube 4. The safety valve sheet 1 includes a covering state being capable of covering the safety valve hole 3 and an opening state being capable of opening the safety valve hole 3. In the technical solution, the plurality of exhaust holes are arranged at intervals around the safety valve hole, so that after the breathing tube is connected to an air cavity cover of the breathing mask, the safety valve sheet will cover the safety valve hole during normal inspiration and expiration of a user through the breathing mask. At the moment, exhaust gas expired by the user will be exhausted from the plurality of exhaust holes around the safety valve hole, thus realizing low-flow exhaust and then reducing exhaust noise. In addition, it is not necessary to arrange an additional exhaust structure on the breathing tube of the breathing mask, so that the breathing tube is simple in structure, and a plastic mold for manufacturing the breathing tube is simple in structure, thus reducing an industrial cost, further simplifying a structure of the breathing mask, and reducing a cost. For example, when the ventilator has a single failure or a conduit of the ventilator is blocked, the safety valve sheet may be converted from the covering state to the opening state. For example, the safety valve sheet is recovered to the opening state (stretched state) under an elasticity, so as to open all the exhaust holes, so that the patient may breathe through all the exhaust holes and the safety valve hole (as shown in FIG. 19 and FIG. 22) to prevent suffocation.

The safety valve hole 3 and the plurality of exhaust holes 11 arranged at intervals around the safety valve hole 3 which are formed in the tube wall of the breathing tube 4 may be manufactured by one mold slider, thus reducing a production cost.

It should be understood here that, in the breathing tube assembly, the exhaust holes 11 may be in various shapes and arranged in various ways. For example, as shown in FIG. 17 to FIG. 19, the exhaust holes 11 are circular holes. Further, the exhaust holes 11 are small holes. Alternatively, as shown in FIG. 20 to FIG. 22, the exhaust holes 11 are strip holes. Certainly, the shape of the exhaust holes 11 is not limited to this, and the arrangement way of the plurality of exhaust holes 11 is not limited to the way shown in FIG. 17 and FIG. 20.

In addition, as shown in FIG. 18, in a direction from inside to outside of the breathing tube 4, diameters of the exhaust holes 11 are gradually increased to form gradually enlarged holes, so that a flow rate of exhaust gas can be slowed down, thus further reducing exhaust noise. In addition, in the covering state, an exhaust gap 9 is formed between an outer side surface 6 of the safety valve sheet 1 and a hole edge 8 of the safety valve hole 3. In this way, as described above, the exhaust gas may also be exhausted through the exhaust gap 9. The exhaust gap 9, for example, may be formed between the outer side surface 6 and the hole edge 8 of the safety valve hole 3 through the protrusion above.

Figure 23:
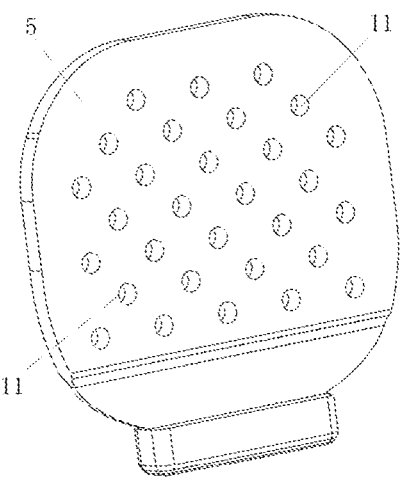
FIG. 23 is a schematic structural diagram of a second safety valve sheet provided by a specific embodiment of the present disclosure.
Figure 24:
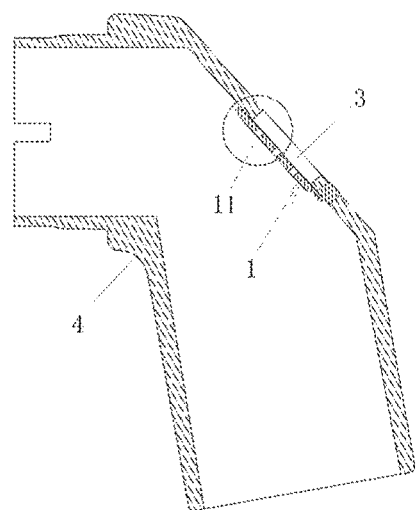
FIG. 24 is a cross-sectional structural diagram of a seventh breathing tube assembly provided by a specific embodiment of the present disclosure, wherein the safety valve sheet is in the covering state, and shows the safety valve sheet in FIG. 23.
Figure 25:
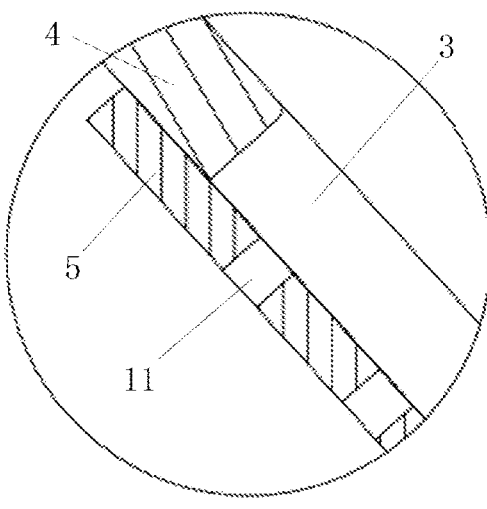
FIG. 25 is an enlarged view of a circle part in FIG. 24.
Figure 26:
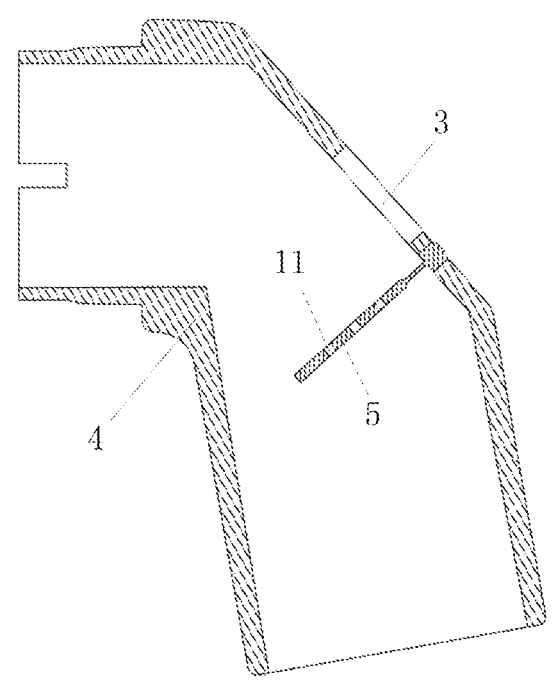
FIG. 26 is a schematic diagram of the safety valve sheet in FIG. 24 in the opening state.

In a sixth aspect, the present disclosure provides a safety valve sheet. With reference to FIG. 23, the safety valve sheet 1 is used for being arranged in a breathing tube 4 which is provided with a safety valve hole 3 in a breathing mask 2. The safety valve sheet includes a sheet body 5 being capable of covering the safety valve hole 3, and a plurality of exhaust holes 11 arranged at intervals are formed in the sheet body 5. In the technical solution, the plurality of exhaust holes arranged at intervals are formed in the sheet body, so that after the safety valve sheet is applied to the breathing tube of the breathing mask, the safety valve sheet will cover the safety valve hole during normal inspiration and expiration of a user through the breathing mask. At the moment, exhaust gas expired by the user will be exhausted from the plurality of exhaust holes in the sheet body, thus realizing low-flow exhaust and then reducing exhaust noise. In addition, it is not necessary to arrange an additional exhaust structure on the breathing tube of the breathing mask, so that the breathing tube is simple in structure, and a plastic mold for manufacturing the breathing tube is simple in structure, thus reducing an industrial cost, further simplifying a structure of the breathing mask, and reducing a cost.

In an embodiment, the sheet body 5 may be a rigid body made of a rigid material. At the moment, the aforementioned transitional connecting sheet may have an elasticity, so that in the case of no effect of an air pressure from, for example, a ventilator, the sheet body 5 may be automatically and elastically recovered from a covering state of covering the safety valve hole to an opening state of opening the safety valve hole, such as converting from the state shown in FIG. 5 to the state shown in FIG. 7.

In another embodiment, the sheet body 5 is a flexible body. For example, the aforementioned clamping block for connection and the aforementioned transitional connecting sheet are integrally formed with the sheet body 5 into the flexible body. For example, the flexible body may be made of a flexible material such as silica gel, or the flexible body may be a flexible elastic sheet having a surface layer covered with soft rubber. In this way, the flexible body, such as the soft silica gel or the soft rubber surface layer of the flexible elastic sheet, can slow down air flow vibration, thus further reducing the exhaust noise.

In addition, the plurality of exhaust holes 11 arranged at intervals which are formed in the sheet body 5 may be in any shape, such as circular holes or strip gaps, and are arranged in various ways.

In a seventh aspect, the present disclosure provides a breathing tube assembly. The breathing tube assembly includes a breathing tube 4 and any safety valve sheet 1 in the sixth aspect above. A safety valve hole 3 is formed in a tube wall of the breathing tube 4, and the safety valve sheet 1 is capable of being movably arranged in the breathing tube 4. The safety valve sheet 1 includes a covering state being capable of covering the safety valve hole 3 and an opening state being capable of opening the safety valve hole 3. In this way, as described above, the exhaust gas expired by the user will be exhausted from the plurality of exhaust holes in the sheet body, thus realizing low-flow exhaust and then reducing exhaust noise. In addition, it is not necessary to arrange an additional exhaust structure on the breathing tube of the breathing mask, so that the breathing tube is simple in structure, and a plastic mold for manufacturing the breathing tube is simple in structure, thus reducing an industrial cost, further simplifying a structure of the breathing mask, and reducing a cost. For example, when the ventilator has a single failure or a conduit of the ventilator is blocked, the safety valve sheet may be converted from the covering state to the opening state. For example, the safety valve sheet is recovered to the opening state (stretched state) under an elasticity, so as to open all the exhaust holes, so that the patient may breathe through the safety valve hole (as shown in FIG. 19 and FIG. 22) to prevent suffocation.

Further, in the covering state, an exhaust gap 9 is formed between an outer side surface 6 of the safety valve sheet 1 and a hole edge 8 of the safety valve hole 3. In this way, as described above, the exhaust gas may also be exhausted through the exhaust gap 9. The exhaust gap 9, for example, may be formed between the outer side surface 6 and the hole edge 8 of the safety valve hole 3 through the protrusion above.

In an eighth aspect, with reference to FIG. 27, the present disclosure provides a breathing mask 2. The breathing mask 2 includes an air cavity cover 10 and a breathing tube assembly 12. The breathing tube assembly 12 is any breathing tube assembly in the third aspect above; or, the breathing tube assembly 12 is any breathing tube assembly in the fourth aspect above; or, the breathing tube assembly 12 is any breathing tube assembly in the fifth aspect above; or, the breathing tube assembly 12 is any breathing tube assembly in the seventh aspect above, wherein one end of the breathing tube 4 is connected to the air cavity cover 10, and the other end of the breathing tube 4 is used for being connected to a pressure support device such as a ventilator. In this way, as described above, the breathing mask is simple in structure and can effectively reduce exhaust noise.

In addition, as shown in FIG. 27, the breathing mask 2 includes a mask frame 15, and the mask frame 15 plays roles of fixing and being connected to a head band during usage. The breathing tube 4, such as a bent tube 4, is connected to a ductus of the ventilator and can rotate around the mask frame 15 during usage. The mask frame 15 is provided with a forehead pad 13 and a liner 14. The air cavity cover 10 may be arranged on the mask frame 15, or a part of the mask frame 15 forms the air cavity cover 10.

The preferred embodiments of the present disclosure are described in detail above with reference to the drawings, but the present disclosure is not limited to this. Within the scope of the technical concept of the present disclosure, many simple modifications may be made to the technical solutions of the present disclosure, including combinations of all specific technical features in any suitable way. In order to avoid unnecessary repetition, various possible combinations will not be explained separately in the present disclosure.

However, these simple modifications and combinations should also be regarded as the contents disclosed by the present disclosure, and all belong to the scope of protection of the present disclosure.

What is claimed is:

1. A breathing tube assembly, comprising a breathing tube and a safety valve sheet, wherein a safety valve hole is formed in a tube wall of the breathing tube, and the safety valve sheet is capable of being movably arranged in the breathing tube; and the safety valve sheet comprises a covering state being capable of covering the safety valve hole and an opening state being capable of opening the safety valve hole; wherein, in the covering state, an exhaust gap is arranged between the safety valve sheet and a hole edge of the safety valve hole;

wherein the safety valve sheet comprises a sheet body, and the sheet body comprises an outer side surface being capable of covering the safety valve hole, wherein a plurality of protrusions are formed on the outer side surface, and the plurality of protrusions are used for being contacted with an inner side surface of the hole edge of the safety valve hole when the sheet body covers the safety valve hole to form a plurality of exhaust gaps between the outer side surface and the hole edge; and/or, the plurality of protrusions are formed on the inner side surface of the hole edge of the safety valve hole, and the plurality of protrusions are used for being contacted with an outer side surface of a safety valve sheet when the safety valve sheet covers the safety valve hole inside the breathing tube to form a plurality of exhaust gaps between the outer side surface and the hole edge, wherein the plurality of protrusions are provided and arranged at intervals along a circumferential direction of the hole edge.

2. The breathing tube assembly according to claim 1, wherein the safety valve sheet is used for being arranged in a breathing tube which is provided with a safety valve hole of a breathing mask.

3. The breathing tube assembly according to claim 2, wherein the sheet body is a flexible body.

4. The breathing tube assembly according to claim 2, wherein a height of the protrusion relative to the outer side surface ranges from 0.1 mm to 1.2 mm.

5. The breathing tube assembly according to claim 4, wherein the plurality of protrusions are provided and arranged at intervals.

6. A breathing mask, comprising an air cavity cover and a breathing tube assembly, wherein the breathing tube assembly is the breathing tube assembly according to claim 1, wherein one end of the breathing tube is connected to the air cavity cover.

7. The breathing tube assembly according to claim 1, wherein the breathing tube is used for being connected to an air cavity cover of a breathing mask, wherein a safety valve hole is formed in a tube wall of the breathing tube.

8. The breathing tube assembly according to claim 1, wherein the breathing tube is used for being connected to an air cavity cover of a breathing mask, wherein a safety valve hole is formed in a tube wall of the breathing tube, a protrusion is formed on an inner side surface of a hole edge of the safety valve hole, and the protrusion is used for being contacted with an outer side surface of a safety valve sheet when the safety valve sheet covers the safety valve hole inside the breathing tube to form an exhaust gap between the outer side surface and the hole edge; and a height of the protrusion relative to the inner side surface of the hole edge ranges from 0.1 mm to 1.2 mm.

9. A breathing tube assembly, comprising a breathing tube and a safety valve sheet, wherein a safety valve hole and a plurality of exhaust holes arranged at intervals around the safety valve hole are formed in a tube wall of the breathing tube, and the safety valve sheet is capable of being movably arranged in the breathing tube; and the safety valve sheet comprises a covering state capable of covering the safety valve hole and an opening state capable of opening the safety valve hole; and in the covering state, a plurality of exhaust gaps are formed between an outer side surface of the safety valve sheet and a hole edge of the safety valve hole; and the safety valve sheet comprises a covering state being capable of covering at least some of the exhaust holes and an opening state being capable of opening the covered exhaust holes.

10. The breathing tube assembly according to claim 9, wherein the exhaust holes are circular holes or strip holes.

11. A breathing tube assembly, comprising a breathing tube and a safety valve sheet, wherein the safety valve sheet is used for being arranged in a breathing tube which is provided with a safety valve hole of a breathing mask, wherein the safety valve sheet comprises a sheet body being capable of covering the safety valve hole, and a plurality of exhaust holes are through holes arranged at intervals are formed in the sheet body; a safety valve hole is formed in a tube wall of the breathing tube, and the safety valve sheet is capable of being movably arranged in the breathing tube; and the safety valve sheet comprises a covering state capable of covering the safety valve hole and an opening state capable of opening the safety valve hole; and in the covering state, a plurality of exhaust gaps are formed between an outer side surface of the safety valve sheet and a hole edge of the safety valve hole;

wherein the plurality of exhaust holes are arranged inside a portion where the safety valve sheet contacts the hole edge of the safety valve hole.

12. The breathing tube assembly according to claim 11, wherein the sheet body is a flexible body.

\*   \*   \*   \*   \*